United States Patent
Freeman et al.

(10) Patent No.: US 10,188,582 B2
(45) Date of Patent: Jan. 29, 2019

(54) OUT OF PHASE CHEST COMPRESSION AND VENTILATION

(71) Applicant: ZOLL Medical Corporation, Chelmsford, MA (US)

(72) Inventors: Gary A. Freeman, Newton Center, MA (US); Christopher Luke Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 710 days.

(21) Appl. No.: 13/970,051

(22) Filed: Aug. 19, 2013

(65) Prior Publication Data
US 2014/0052032 A1    Feb. 20, 2014

Related U.S. Application Data

(60) Provisional application No. 61/684,487, filed on Aug. 17, 2012.

(51) Int. Cl.
*A61H 31/00* (2006.01)
*A61N 1/39* (2006.01)
(Continued)

(52) U.S. Cl.
CPC ......... *A61H 31/006* (2013.01); *A61H 31/005* (2013.01); *A61H 31/007* (2013.01);
(Continued)

(58) Field of Classification Search
CPC .... A61H 31/00; A61H 31/004; A61H 31/005; A61H 31/006; A61H 31/007; A61H 31/008; A61H 2201/1253; A61H 31/02
(Continued)

(56) References Cited

U.S. PATENT DOCUMENTS 1,175,671 A * 3/1916 Acklen ................. A61H 31/02
601/44
2,490,395 A * 12/1949 Wilm .................... A61H 31/02
601/44
(Continued)

FOREIGN PATENT DOCUMENTS

| EP | 2343097 A2 | 7/2011 |
|---|---|---|
| GB | 1140581 A | 1/1969 |
| WO | 9817224 A1 | 4/1998 |

OTHER PUBLICATIONS

Christenson, J.M., D.R. Hamilton, N.W. Scott-Douglas, J.V. Tyberg, and D.G. Powell. "Abdominal Compressions During CPR: Hemodynamic Effects of Altering Timing and Force." The Journal of Emergency Medicine 10.3 (1992): 257-66.*

(Continued)

*Primary Examiner* — Michael Tsai
*Assistant Examiner* — Christopher Miller
(74) *Attorney, Agent, or Firm* — Zoll Medical Corporation

(57) ABSTRACT

A method for providing emergency care to a patient of an adverse cardiac event is disclosed that includes causing multiple chest compressions to be provided to the patient, and causing multiple inducements of ventilation to be provided to the patient. Particular ones of the multiple chest compressions can overlap time-wise with corresponding ones of the multiple inducements of ventilation, and can be substantially out of phase with the corresponding ones of the multiple inducements of ventilation.

24 Claims, 7 Drawing Sheets

(51) Int. Cl.
*G06F 19/00* (2018.01)
*A61H 11/00* (2006.01)

(52) U.S. Cl.
CPC .......... *A61N 1/39* (2013.01); *A61H 2011/005* (2013.01); *A61H 2201/0157* (2013.01); *A61H 2201/1215* (2013.01); *A61H 2201/1238* (2013.01); *A61H 2201/501* (2013.01); *A61H 2201/5012* (2013.01); *A61H 2201/5015* (2013.01); *A61H 2201/5046* (2013.01); *A61H 2201/5076* (2013.01); *A61H 2201/5084* (2013.01); *A61H 2201/5097* (2013.01); *A61H 2230/045* (2013.01); *G06F 19/3481* (2013.01)

(58) Field of Classification Search
USPC .................................................. 601/41–44
See application file for complete search history.

(56) References Cited

U.S. PATENT DOCUMENTS

| | | | | |
|---|---|---|---|---|
| 3,509,899 A * | 5/1970 | Hewson | A61H 31/006 | 128/202.16 |
| 4,326,507 A * | 4/1982 | Barkalow | A61H 31/006 | 601/106 |
| 4,349,015 A * | 9/1982 | Alferness | A61H 9/0078 | 128/205.16 |
| 4,397,306 A * | 8/1983 | Weisfeldt | A61H 9/0078 | 601/41 |
| 4,753,226 A * | 6/1988 | Zheng | A61H 9/0078 | 601/150 |
| 4,863,385 A * | 9/1989 | Pierce | G09B 23/288 | 434/265 |
| 4,928,674 A * | 5/1990 | Halperin | A61H 9/0078 | 600/495 |
| 5,398,676 A * | 3/1995 | Press | A61M 16/0051 | 128/204.18 |
| 5,490,820 A * | 2/1996 | Schock | A61H 9/0078 | 601/1 |
| 5,492,115 A * | 2/1996 | Abramov | A61H 31/00 | 128/205.24 |
| 5,496,257 A * | 3/1996 | Kelly | A61H 31/005 | 600/454 |
| 5,630,789 A * | 5/1997 | Schock | A61H 31/00 | 601/1 |
| 5,806,512 A * | 9/1998 | Abramov | A61H 9/0078 | 128/204.18 |
| 5,891,062 A | 4/1999 | Schock et al. | | |
| 6,066,106 A * | 5/2000 | Sherman | A61H 31/006 | 601/134 |
| 6,213,960 B1 | 4/2001 | Sherman et al. | | |
| 6,289,890 B1 * | 9/2001 | Bliss | A61M 16/00 | 128/203.11 |
| 6,312,399 B1 * | 11/2001 | Lurie | A61H 31/00 | 601/41 |
| 6,447,465 B1 * | 9/2002 | Sherman | A61H 31/00 | 601/41 |
| 6,872,080 B2 * | 3/2005 | Pastrick | G09B 23/288 | 434/262 |
| 8,105,249 B2 | 1/2012 | Freeman | | |
| 8,121,681 B2 | 2/2012 | Hampton et al. | | |
| 8,591,439 B1 * | 11/2013 | Flood | A61H 31/00 | 128/205.24 |
| 8,631,790 B1 * | 1/2014 | Di Capua | A61M 16/0051 | 128/204.21 |
| 2003/0135139 A1 * | 7/2003 | Bassuk | A61H 31/005 | 601/41 |
| 2004/0143194 A1 * | 7/2004 | Kihara | A61B 5/1135 | 600/534 |
| 2004/0162585 A1 * | 8/2004 | Elghazzawi | A61N 1/3925 | 607/5 |
| 2005/0165334 A1 * | 7/2005 | Lurie | A61M 16/06 | 601/44 |
| 2005/0165335 A1 | 7/2005 | Sherman et al. | | |
| 2005/0251213 A1 * | 11/2005 | Freeman | G09B 23/288 | 607/5 |
| 2006/0094991 A1 * | 5/2006 | Walker | A61H 31/004 | 601/41 |
| 2006/0161087 A1 | 7/2006 | Carter et al. | | |
| 2007/0270724 A1 * | 11/2007 | Havardsholm | A61H 31/004 | 601/41 |
| 2008/0097257 A1 * | 4/2008 | Stromsnes | A61H 31/00 | 601/41 |
| 2009/0062701 A1 * | 3/2009 | Yannopoulos | A61H 9/0078 | 601/41 |
| 2010/0004571 A1 * | 1/2010 | Nilsson | A61H 31/006 | 601/41 |
| 2010/0185127 A1 * | 7/2010 | Nilsson | A61H 31/004 | 601/41 |
| 2010/0326442 A1 * | 12/2010 | Hamilton | A61H 9/0078 | 128/204.21 |
| 2010/0326443 A1 * | 12/2010 | Steen | A61M 16/04 | 128/204.23 |
| 2011/0098611 A1 | 4/2011 | Flood | | |
| 2011/0201979 A1 * | 8/2011 | Voss | A61H 31/005 | 601/41 |
| 2011/0202100 A1 * | 8/2011 | Tan | A61H 31/005 | 607/6 |
| 2011/0295163 A1 * | 12/2011 | Vijayanagar | A61F 7/02 | 601/18 |
| 2012/0016179 A1 * | 1/2012 | Paradis | A61H 9/0078 | 600/17 |
| 2013/0338550 A1 * | 12/2013 | Faller | A61H 31/006 | 601/41 |

OTHER PUBLICATIONS

International Search Report & Written Opinion, PCT/US2013/55593, dated Nov. 22, 2013, 11 pages.

* cited by examiner

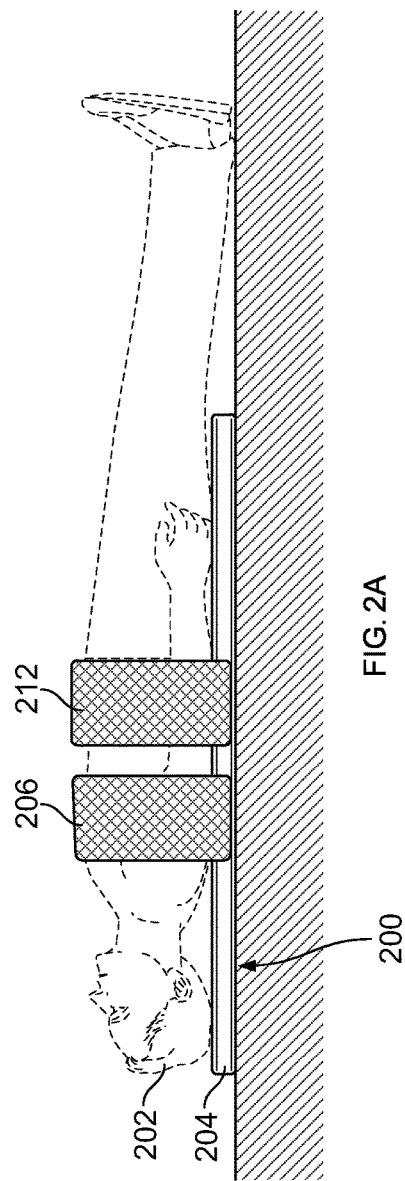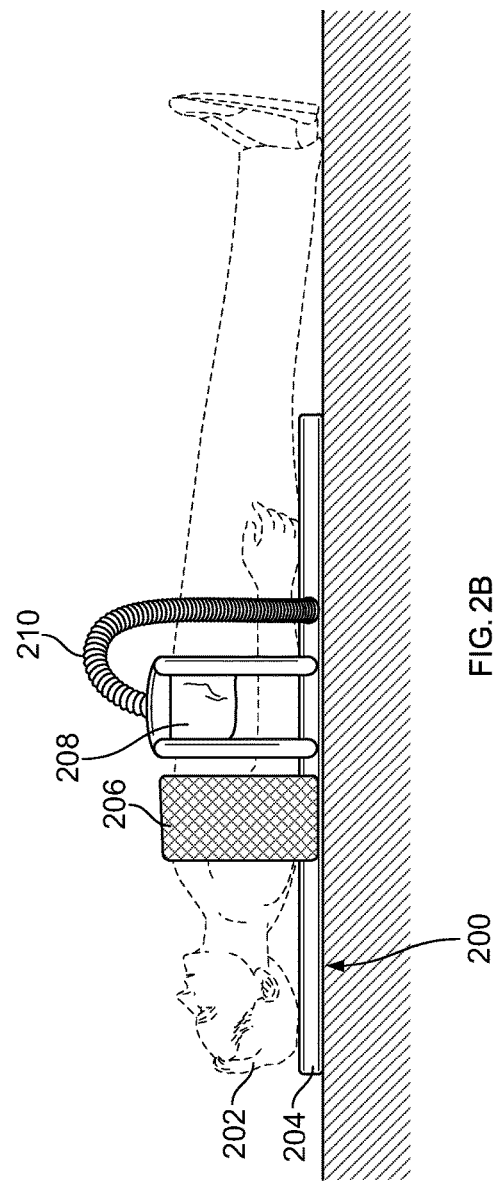

OUT OF PHASE CHEST COMPRESSION AND VENTILATION

CLAIM OF PRIORITY

This application claims priority under 35 USC § 119(e) to U.S. Patent Application Ser. No. 61/684,487, filed on Aug. 17, 2012, the entire contents of which are hereby incorporated by reference.

TECHNICAL FIELD

This document relates to cardiac resuscitation, and in particular to systems and techniques for assisting rescuers in performing cardio-pulmonary resuscitation (CPR).

BACKGROUND

CPR is a process by which one or more rescuers may provide chest compressions and ventilation to a patient who has suffered an adverse cardiac event—by popular terms, a heart attack. Chest compressions are considered to be the most important element of CPR during the first five to eight minutes after CPR efforts begin, because chest compressions help maintain circulation through the body and in the heart itself, which is the organ that can sustain the most damage from an adverse cardiac event. Generally, American Heart Association CPR Guidelines define protocols by which a rescuer is to apply the chest compressions in coordination with ventilations. For example, current 2010 AHA Guidelines specify a ratio of 30:2 for compressions to ventilations—i.e., thirty compressions for every two breaths. And compressions are to be performed at a rate of around 100 per minute.

CPR may be performed by a team of one or more rescuers, particularly when the rescuers are professionals such as emergency medical technicians (EMTs) on an ambulance crew. One rescuer can provide the chest compressions and another can time their ventilations of the patient to match the chest compressions according to the appropriate CPR protocol. When professionals such as EMTs provide the care, ventilation is more likely to be provided via a ventilation bag that a rescuer squeezes, than by mouth-to-mouth.

The CPR can be performed in conjunction with providing shocks to the patient from an external defibrillator, including from an automatic external defibrillator (AED) that is designed to be used by laypeople. Such AEDs often provide audible information to rescuers such as "push harder" (when the rescuer is not performing chest compressions forcefully enough), "stop CPR," "stand back" (because a shock is about to be delivered), and the like. In determining how chest compressions are being performed, certain defibrillators may obtain information from one or more accelerometers (such as in the CPR D PADZ, CPR STAT PADZ, and ONE STEP pads (made by ZOLL MEDICAL of Chelmsford, Mass.) that can be used to compute depths of chest compression, e.g., to determine that the compressions are too shallow to be effective and thus to cause the defibrillator to speak the verbal cue "push header."

Chest compressions and ventilation may also be provided mechanically. For example, the AUTOPULSE non-invasive cardiac support pump (made by ZOLL MEDICAL of Chelmsford, Mass.) includes a back board and belt that wraps around a patient's chest. A motor in the backboard causes the belt to cycle between tightening and loosening around the patient's chest so as to provide chest compressions automatically and periodically. Automatic ventilation has been provided to people with various respiratory problems by means of devices like a cuirass, in the form of a shell that wraps around a patient's torso and applies negative pressure below their diaphragm, such as in the form of the HAYEK RTX respirator from Medivent International Ltd. of London, UK.

SUMMARY

This document describes systems and techniques that may be used to help deliver coordinated CPR chest compressions and ventilation to a patient in need of emergency assistance. In typical application of chest compressions, a significant amount of blood flows in a direction opposite to that desired. That is, during the compression downstroke, when blood should be flowing from the right side of the heart into the lungs for re-oxygenation, it is instead flowing in a retrograde fashion on the venous side from the thorax back into the abdomen. One factor for this retrograde flow during the compression downstroke is the increased vascular resistance of the lungs. But when abdominal compressions are properly coordinated with chest compressions, the vascular resistance of the lungs can be overcome, and retrograde flow during the compression downstroke can be reduced.

The compressions occur according to a repeating cycle that repeats according to the steps: act-hold-release-hold. For example, for chest compressions, a rescuer or device may push downward on a patient to compress the chest (act), may hold briefly at a bottom position, and may then release and wait briefly (hold) before compressing again—in a typical and well-known chest compression cycle. To maximize the effectiveness of the chest compressions, an abdominal compression may begin slightly before the chest compression begins, such that the compress-hold-release cycle for the abdominal compression is partially completed before the chest compression begins. The properly-timed compression on the abdomen will minimize the amount of blood flowing back into the abdomen during the compression down stroke. This particular timing for what may be termed abdominal counter pulsation causes abdominal compressions to be coordinated to coincide the early down stroke of chest compressions (rather than with the early relaxation phase) to reduce retrograde flow and enhance blood flow into the lungs for reoxygenation.

The cycle generally has a constant periodicity, but the periodicity may be changed as a rescue attempt continues. For example, venous congestion may increase over time during a rescue operation, so that chest compressions need to become more aggressive over time to push the blood out of the heart and through the patient's body. As a result, the parameters of the chest and abdominal compressions may be varied, including the depth of compression, the periodicity of the cycles, the speed of compression and release, the "dwell" period for any compression, and the relative phasing of the two types of compressions. For example, while the chest compression may at first start when the abdominal compression is one-quarter complete, so that the chest compression trails the abdominal compression by 90 degrees in phase, the phase difference may be caused to increase over time as the rescue continues so that compression on the abdomen is exerting less backpressure to the chest compression at the beginning of the phase of the chest compression.

Vascular resistance of the lungs may also be reduced by providing negative pressure ventilation of the lungs during CPR. Current methods for ventilation during CPR are provided by various methods of positive pressure ventilation such as those delivered by what is termed a bag-valve-mask combination with which a mask is placed over the victim's mouth and nose, and air is forced into the victim's lungs by squeezing the ventilator bag. The bag may be replaced by various forms of mechanically-powered ventilator devices. Unfortunately, any form of positive pressure ventilation increases the vascular resistance of the lungs, thus reducing forward blood flow from the right side of the heart into the lungs for reoxygenation.

As described below, negative pressure ventilation may be provided to reduce lung vascular resistance. Negative pressure ventilation may be provided by negative pressure on the abdomen rather than positive pressure. For example, a cuirass may be wrapped around the abdomen and may pull outward on the abdomen, thereby pulling the patient's diaphragm downward, and thereby causing the lungs to fill with air. The ventilations are delivered at a much slower rate than the compressions, for example one ventilation for every ten or so compressions. Negative pressure will be generated around the abdomen every tenth or so compression to cause air to enter the lungs. In some embodiments, the cuirass may also be capable of generating positive pressure to squeeze the abdomen synchronized to the compressions as described above. The cuirass may also incorporate a mechanical compression element that presses the abdomen independent of the negative or positive pressure that the cuirass generates.

In certain implementations, such systems and technique may provide one or more advantages. For example, a patient may be provided with improved circulation of blood through the patient's lungs and the rest of the patient's body. As a result, the patient's tissue main remain oxygenated for a longer period, and death of the tissue and of the patient may be lessened or eliminated.

In one implementation, a method for providing emergency care to a patient of an adverse cardiac event is disclosed. The method comprises causing multiple chest compressions to be provided to the patient, and causing multiple inducements of ventilation to be provided to the patient, wherein particular ones of the multiple chest compressions are controlled to overlap time-wise with corresponding ones of the multiple inducements of ventilation, and are substantially out of phase with the corresponding ones of the multiple inducements of ventilation. In one example, the chest compressions and the inducements of ventilation are performed at substantially constant rates that substantially match each other. Also, each of the particular ones of the chest compressions can begin while the corresponding ones of the inducements of ventilation are occurring, or when the corresponding ones of the inducements of ventilation are about one-quarter complete. Similarly, each of the particular ones of the chest compressions are performed approximately 90 or 270 degrees out of phase with the corresponding ones of the inducements of ventilation.

In certain aspects, downward force on the patient's chest is applied for each of the particular ones of the chest compressions while downward force is removed from the patient's abdomen during the corresponding ones of the inducements of ventilation. Also, the multiple chest compressions can be provided by an automatic chest compression unit and the multiple inducements of ventilation are provided by an automatic mechanical ventilator. The chest compression unit can comprise a belt wrapped around the patient's chest or a piston pressing against the patient's chest, and the automatic mechanical ventilator comprises a cuirass. Moreover, the method can include automatically adaptively varying parameters of the chest compressions, the inducements of ventilation, or both, in response to electronically monitoring a condition of the patient while the chest compressions are provided to the patient. The automatically adaptively varying parameters of the chest compressions can also comprise changing a manner in which the chest compressions, inducements of ventilation, or both, are provided to the patient, measuring a resulting change in one or more patient-dependent parameters, and selecting new parameters for provision of chest compression, inducements of ventilation, or both based on the measured resulting change.

In another implementation, a system for providing coordinated chest compressions and ventilation to a medical patient is disclosed. The system comprises a substrate arranged to press against a patient, a chest compressor attached to the substrate and positioned to provide chest compressions to the patient, and a mechanical ventilator attached to the substrate and positioned to engage the patient at the abdomen to induce ventilations of the patient. The system can also include an electronic controller programmed to actuate the chest compressor and the mechanical ventilator so as to align chest compressions of the patient and ventilation of the patient in a predetermined manner. The electronic controller can be programmed to cause the chest compressions and ventilation to be performed at substantially constant rates that substantially match each other. Also, each of particular ones of the chest compressions can begin while corresponding ones of the ventilations are already occurring, and the controller can be programmed so that each of the particular ones of the chest compressions begin when the corresponding ones of the ventilations are about one-quarter complete, or that each of the particular ones of the chest compressions are performed approximately 90 or 270 degrees out of phase with the corresponding ones of the ventilations. Moreover, downward force on the patient's chest can be applied for each of the particular ones of the chest compressions while downward force is removed from the patient's abdomen during the corresponding ones of the ventilations.

In some aspects, the mechanical ventilator comprises a cuirass. Moreover, the chest compressor can comprise a belt positioned to wrap around the patient's chest and to be shortened in order to apply chest compressions to the patient. The cuirass can be pneumatically powered, and can receive pneumatic power from a mechanism that is mechanically couple to a motor that drives the belt. Moreover, the electronic programmer can be programmed to automatically adaptively vary parameters of the chest compressions, the ventilations, or both, in response to electronically monitoring a condition of the patient while the chest compressions are provided to the patient.

Other features and advantages will be apparent from the description and drawings, and from the claims.

DESCRIPTION OF DRAWINGS

FIGS. 2A and 2B show a side view of a patient being treated by mechanisms for performing coordinated chest compressions and abdominal-based ventilations.

DETAILED DESCRIPTION

Figure 1:
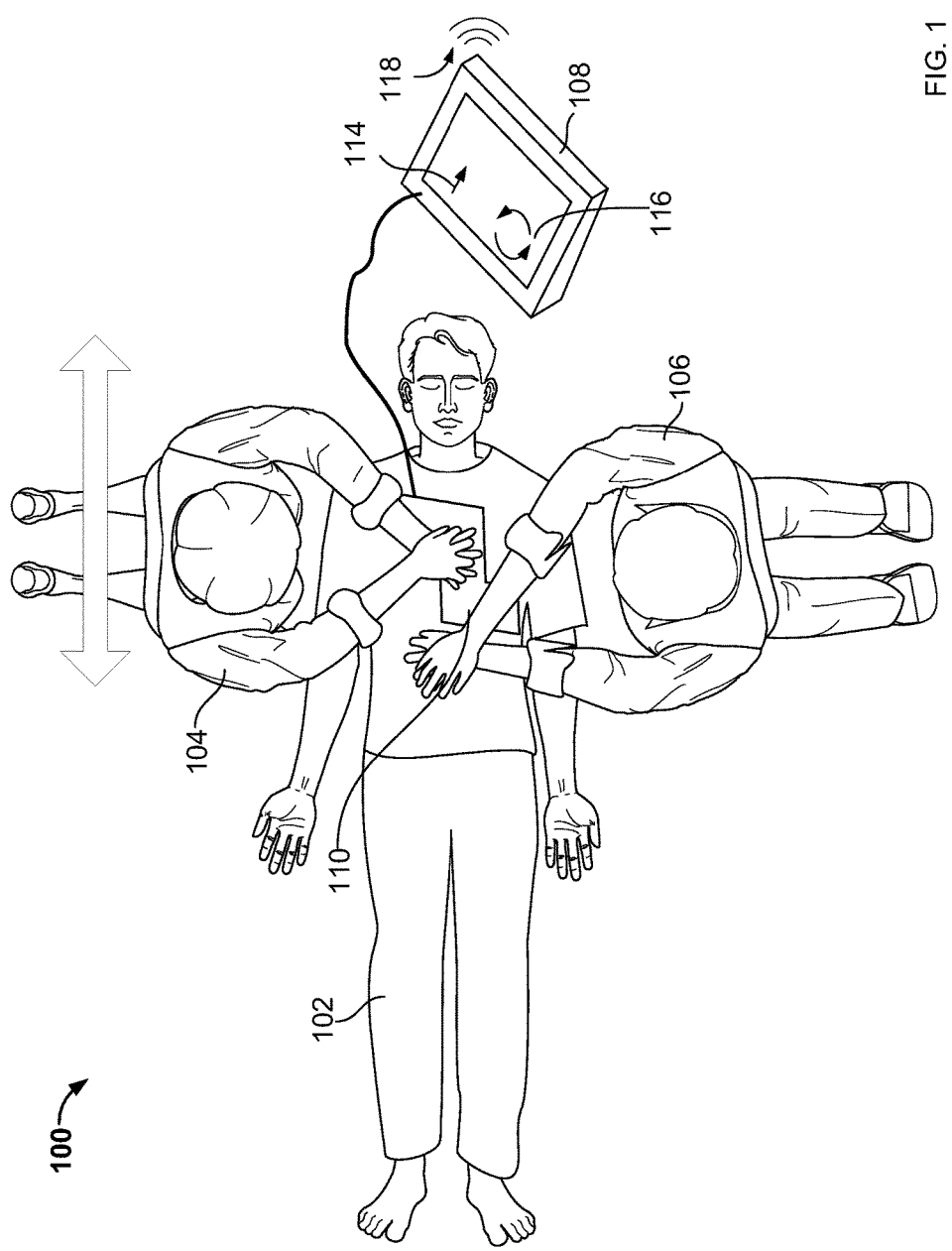
FIG. 1 is an overhead view of rescuers performing CPR on a patient using an electronic system that instructs them in performance of the CPR.

This description discusses systems and techniques for guiding the provision of care to a patient, such as the provision of CPR to a patient who has suffered cardiac arrest. For example, a portable electronic defibrillator may be provided to rescuers and may include common features for delivering defibrillating energy (a shock) to a patient suffering from cardiac arrest through electrodes that may be placed on the torso of the patient. The defibrillator may also be provided with a mechanism for sensing the manner in which CPR chest compressions are performed on the patient, such as a puck or similar item that includes an accelerometer, and that may be placed under the hands of the person performing chest compressions and on top of the sternum of the patient. The defibrillator may use information from such an item to identify the depth, rate, and timing of chest compressions that are being performed by a rescuer.

The system may further provide mechanisms for directing the user in performing the compressions, and other mechanisms for directing another user in compressing an abdominal area of the patient that is below the chest area, where the dividing line between the chest area and the abdominal area is defined by a location of the patient's diaphragm—though generally, it will be preferred to provide the forces discussed here at a certain minimum distance above and below the diaphragm.

The mechanisms for directing the users in providing compressions may include mechanisms for coordinating the chest compressions with the abdominal compressions, so that they occur in sequence and in a partially overlapping manner. In particular, for example, the system may direct initiation of abdominal compressions slightly in advance of directing initiation of chest compressions, so that the abdominal compressions start first and are still occurring when the chest compressions start. Thus, the chest compressions may be said to be trailing the abdominal compressions slight, such as by 90 degrees, or a quarter of a compress-hold-release sequence, or alternatively, a quarter of an entire compress-hold-release-hold cycle.

Compression of the abdomen may place positive pressure on the lungs, but negative pressure may also be provided. For example, a cuirass may provide negative pressure to the abdomen, and thereby pull the diaphragm downward and apply negative pressure to the outside of the lungs, thereby causing a patient to draw air in. Alternatively, a mechanical device may be applied to the mouth of a patient to provide positive pressure to fill the lungs or negative pressure to empty the lungs, and the provision of such pressure may be coordinated in an out-of-phase arrangement with chest compressions (e.g., with a phase difference substantially different than 0 degrees or 180 degrees), in the manners discussed here.

The directions from the defibrillator to rescuers may occur in various manners, such as by audible prompts that are timed to when the respective rescuer should perform their compressions or other actions (e.g., squeezing a ventilation bag). For example, beeps of different tones may represent an instruction for a respective rescuer to begin his or her compression (where each rescuer is assigned a particular tone). To provide for the chest compressions to be trailing slightly, the pattern may be beep-beep-pause-beep-beep-pause—where the first beep of each cycle is aimed at the person performing abdominal compressions and the second to the person performing chest compressions. Alternatively, the defibrillator may speak words such as "Belly—chest <pause> Belly—chest <pause>", or similar directions that rescuers can easily recognize, remember, and follow, even in a high-stress situation.

FIG. 1 is an overhead view of rescuers 104, 106 performing CPR on a patient 102 using an electronic system that instructs them in performance of the CPR. In this example, rescuers 104, 106 are already in position and providing care to the patient 102, with rescuer 104 in position and providing chest compressions to the torso of the patient 102, and rescuer 106 providing ventilation by compressing the abdominal area of the patient 102. The rescuers 104, 106 may be lay rescuers who were in the vicinity of the patient 102 when the patient 102 first required care, or may be trained medical personnel, such as emergency medical technicians (EMTs). Although two rescuers are shown here for purposes of explanation, additional rescuers may also care for the patient 102, and may be included in a rotation of rescuers providing particular components of care to the patient 102, where the components may include chest compressions, ventilation, administration of drugs, and other provision of care.

In some examples, one or more therapeutic delivery devices (not shown) can automatically deliver the appropriate therapy to the patient. The therapeutic delivery devices can be, for example, a portable automatic chest compression device (e.g., with a belt that wraps around the patient's chest) that may also include an abdominal compression or expansion device, a drug infusion device, an automatic ventilator and/or a device that includes multiple therapies such as defibrillation, chest compression, ventilation, and drug infusion. The therapeutic delivery devices can be physically separate from the defibrillator 108, and control of the therapeutic delivery devices may be accomplished by a communications link from the defibrillator 108 that may be wired, wireless, or both.

In other examples, control and coordination for the overall resuscitation event and the delivery of the various therapies may be accomplished by a device or processing element that is external to the defibrillator 108, such as by use of a tablet-based computer that is controlled by one of the rescuers. For instance, such a device may download and process ECG data from the defibrillator 108; analyze the ECG signals, perform relevant determinations like those discussed above and below based on the analysis, and control the other therapeutic devices. In other examples, the defibrillator 108 may perform all the processing of the ECG, including analyzing the ECG signals, and may transmit to a separate device only the final determination of the appropriate therapy, whereupon the separate device can perform the control actions on the other linked devices.

An electrode assembly 110 is shown in position on the patient 102 in a normal position. The electrode assembly 110, in this example, is an assembly that combines an electrode positioned high on the right side of the patient's torso and an electrode positioned low on the left side of the patient's torso, along with a sensor package located over the patient's sternum. The sensor package, which is obscured in the figure by the hands of rescuer 104 in this example, may include an accelerometer or similar sensor package that may be used in cooperation with a computer in the defibrillator 108 to generate an overall quality score for the chest compression, and the quality score may indicate instantaneous quality or average quality across a time.

The score may indicate when and how the rescuer 104 is performing chest compressions on the patient 102, based on signals from the sensor package. For example, as a simplified description, signals from an accelerometer may be double integrated to identify a vertical displacement of the sensor package, and in turn of the sternum of the patient 102, to identify how deep each chest compression is. The time between receiving such input from the sensor package may be used to identify the pace at which chest compressions are being applied to the patient 102.

The defibrillator 108 in this example is connected to the electrode package 110 and may operate in a familiar manner, e.g., to provide defibrillating shocks to the electrode package 110. As such, the defibrillator may take a generally common form, and may be a professional style defibrillator, such as the R-SERIES, M-SERIES, or E-SERIES from ZOLL Medical Corporation of Chelmsford, Mass., or an automated external defibrillator (AED), including the AED PLUS, or AED PRO from ZOLL Medical Corporation. The defibrillator is shown in one position relative to the rescuers 104, 106 here, but may be placed in other locations to better present information to them, such as in the form of lights, displays, vibrators, or audible sound generators on a chest-mounted component such as an electrode or via an addressable earpiece for each of the rescuers. Such feedback, as discussed more fully below, may be on units that are separate from the main housing of the defibrillator, and that may communication information about the patient 102 and performance of CPR to the defibrillator 108 or may receive feedback information from the defibrillator 108, through either wired or wireless connects that are made directly with the defibrillator 108 or indirectly through another device or devices.

Similar sensing devices may be used in conjunction with an item that may be located under the hands of rescuer 106 who is compressing the abdomen. Such devices may be used to measure the depth and rate of compression by rescuer 106 in attempting to induce ventilations via motion of the patient' abdominal region, and may employ accelerometers in a manner to that just discussed, in doing so. Such devices may both help the rescuer position his or her hands properly, and also sense whether the rescuer is performing the necessary actions properly so as to provide feedback to the rescuer as discussed above and below.

For illustrative purposes, two particular examples of feedback are shown here on a display of the defibrillator 108. First, a power arrow 114 provides feedback to the rescuer 104 regarding the depth of compression that the rescuer 104 is applying in each compression cycle to the patient 102. In this example, power arrow 114 is pointing upward, and thus indicating to rescuer 104, that rescuer 104 needs to apply more vigorous input to create deeper chest compressions. Such feedback may be only provided visually for performing chest compressions, in order to minimize the amount of information that the rescuer 104 must deal with in a stressful situation. For example, an arrow indicating to apply less compression may not be shown under an assumption that very few rescuers will apply too much compression, and thus the user need only respond to indications to apply more pressure. The particular type of feedback to be provided can be determined by a designer of the defibrillator 108 and may vary to match particular situations and implementations.

Separately, the rescuer 104 may be provided with additional limited feedback, such as feedback for performing chest compressions at an appropriate rate. As one example, the defibrillator 108 may emit a sound through speaker 118 in the form of a metronome to guide the rescuer 104 in the proper rate of applying CPR. A visual representation may also indicate rates for performing compressions, such as a blinking of the display on defibrillator 108. In addition, or as an alternative output mechanism that is designed to avoid distracting rescuer 106, haptic feedback may be provided to rescuer 104 through electrode assembly 110.

For example, a puck or other item on which the rescuer 104 places her hands may be provided with mechanisms for vibrating the puck similar to mechanisms provided for vibrating portable communication devices (e.g., when an incoming telephone call is received on a smartphone). Such vibrating may be provided so as to minimize the amount of information that can distract other rescuers in the area, and may also more directly be used by the rescuer 104 to synchronize her chest compression activities with the output. For example, the vibrations may be periodic (approximate 100 times per minute) at the rate of performing chest compressions when the rescuer 104 should be performing compressions and may stop or be vibrated constantly when the rescuer 104 is to stop and switch positions with another rescuer, such as rescuer 106. With feedback provided at the rescuer's hands, and because the rescuer 104 is providing the chest compressions with her hands directly, input by the system into her hands may be more directly applied with respect to the rescuer 104 keeping an appropriate pace. Such haptic feedback may also relieve the rescuer 104 of having to turn her head to view the display on defibrillator 108. Thus, a first type of feedback, such as pulsed visual, audible, or tactile feedback may be provided to guide a user in performing CPR, and that type of feedback may be interrupted and replaced with a different type of feedback such as constant sound or vibration to indicate that a rescuer is to stop performing the particular component of CPR and let someone else take over.

Similar feedback may be provided to rescuer 106 in providing abdominal compressions. For example, an image of a patient may be shown on the defibrillator 108 display, and separate power arrows, like that just discussed, may be shown, respectively, over the patient's chest and over the patient's abdomen. Each rescuer 104, 106 may then be able to see whether they are providing the right effort and also acting at the right time.

Feedback may also, or alternatively, be provided audibly, as discussed above. For example, two different tones—one for the rescuer 104 and one for the rescuer 106—may be generated at different sound frequencies and at the time at which the system wants to trigger the respective rescuer 104, 106 to perform a compressive action. Also, the defibrillator may speak words, such as "belly" to trigger compression by rescuer 106, and "chest" to trigger compression by rescuer 104. The defibrillator may determine that one or the other of rescuers 104, 106 act more quickly or more slowly than desired in response to the audible or visible prompts, and may change the timing of the prompts to adjust for such inaccurate reaction times by the one or more rescuers. For example, if abdominal compressions are supposed to lead chest compressions by 90 degrees, and the defibrillator 108 senses, via the mechanisms described above, that the lag is only 80 degrees (because the rescuer 104 has slower reaction time than does rescuer 106), the system may move the audible prompts apart in time so that the delay between them is equivalent to 100 degrees of a cycle, thus inducing the rescuers 104, 106 to be properly 90 degrees apart in their real actions on the patient 102.

Cycling arrows 116 are shown separately on the display of the defibrillator 108. Such arrows may indicate to the rescuer 104 and to the rescuer 106 that it is time for them to switch tasks, such that rescuer 104 begins providing abdominal compressions (which might be physically easier)—as shown by the arrow superimposed over the legs of rescuer 104 to indicate that she would slide upward toward the patient's abdomen—and rescuer 106 begins providing chest compressions on electrode assembly 110. Where there are three or more rescuers, the third rescuer may have been resting, and may take over chest compressions for rescuer 104 when a rescuer change is directed by the system, and the rescuer 104 may then rest or may provide abdominal compressions while rescuer 106 rests or does something else. For example, the rescuers may readily determine that rescuer 106 does not have the strength to provide consistent chest compressions on the patient 102, and may determine that rescuer 106 should constantly provide abdominal compressions, while other rescuers switch out in providing chest compressions. Thus, when the arrows 116 are displayed, rescuer 106 may stay in place while two other rescuers switch places with respect to delivering chest compressions. In the examples discussed here, the system may be programmed to be indifferent to the manner in which rescuers decide to rotate, and the rotation may change during a rescue (e.g., rescuer 106 may initially provide chest compressions as part of a 3-person rotation and may then bow out and just provide ventilation while the other 2 rescuers rotate on chest compressions).

The defibrillator 108 may cause the cycling arrows 116 to be displayed based on the occurrence of various events. In one example, the cycling arrows 116 may be displayed after a set time period has elapsed since rescuer 104 began applying chest compressions. For example, a particular CPR protocol may require switching of rescuers at certain predefined periodic intervals (e.g., every 2 minutes). As described below in more detail, the cycling arrows 116 or a similar cycling signal, may alternatively be generated according to determinations made by the defibrillator 108 regarding the quality of chest compressions being provided to the patient 102 by rescuer 104, including by monitoring past compression parameters (e.g., rate over several compressions and depth) and monitoring the rescuer directly (e.g., by determining a pulse and blood oxygen level of a rescuer). Such an analysis may recognize that rescuers tire progressively over time as they are providing chest compressions, so that the depth of chest compressions is likely to fall over time, and the rate of chest compressions may also fall or become more erratic over time.

The defibrillator 108 may thus be programmed to identify when such factors indicate that the chest compression ability of the rescuer 104 (and/or abdominal compression capability of the rescuer 106) has fallen, or is about to fall, below a level that is of adequate effectiveness. As discussed below, for example, a score may be generated for the depth of compression based on how far from optimal compression each of the rescuer's 104 compressions are. Another score may be generated based on how far from optimal the rate of compressions are, and the two scores (depth and rate) may be combined to generate an overall quality score for each compression. A third score may indicate the rescuer's 104 physical state (e.g., via pulse measurement) and that score may also be combined. A running quality score may then be computed to indicate the quality of compressions over a period of time, such as over the last several compressions made by the user, so as to better indicate a trend in the quality of chest compressions being provided (in the past, the near future, or both). When the quality score falls below a threshold, the defibrillator 108 may then generate an indication that the current rescuer 104 should stop performing chest compressions and allow someone else to take over, such as by displaying cycling arrows 116.

Similarly, the quality of ventilation may be monitored. For example, providers of ventilation may tire. They may be reminded initially, such as by a beeping metronome tied to the proper rate. As with reminders for chest compression, such a reminder may be provided constantly, whether the user is performing properly or not, or can be triggered to start when the user is initially identified as performing in a substandard fashion. Subsequently, if the substandard performance continues for a predetermined time period or deteriorates to a second threshold level; the performance trends in a manner that indicates the user is not likely to improve the performance; or the performance otherwise indicates that the provider of ventilation should be switched out, a switching indication may be generated. Also, whether for compression or ventilation, different colors of lights may be used to indicate different types of feedback, such as a green light for good work, a yellow light to indicate a temporary deviation from good work, and a red light or even a blinking red light to indicate that the rescuer should switch out with someone else.

Where the providers of chest compressions and of ventilation (e.g., via abdominal compression and/or ventilation through a patient's mouth) are both being monitored in such a manner, a signal to switch may be generated when the first provider hits a substandard level. Alternatively, if chest compressions are considered more important than is ventilation, the level at which ventilation will trigger a switch can be set much more below a level considered to be satisfactory as compared to a level for chest compressions. In other words, a system may be biased to let the "weak" rescuer continue performing ventilation, rather than switching to a situation in which a somewhat fresh, but nonetheless tired with respect to squeezing a bag, and weak rescuer is placed in the most important position over another rescuer who may be more tired but is overall stronger at performing chest compressions. Various mechanisms may be used to balance the multiple factors, which include the relative important of each component to patient outcomes, the relative strength of each rescuer, the current performance and trending of performance for each rescuer, and knowledge or performance and trending for each rescuer from prior rescues (e.g., if the rescuers 104, 106 are part of an EMT team that uses the same defibrillator multiple times, or who have their data from multiple rescues uploaded to a central system for analysis) or prior cycles in the same rescue.

The process of observing the quality of a component of the CPR, such as the quality of chest compressions and providing prompts to the users in the relative timing of their performance of chest compressions and abdominal compressions, may then continue recursively as long as care is being provided to the patient 102. For example, after the defibrillator 108 generates an indication to switch providers of chest compression, the defibrillator 108 may sense through the electrode package 110 that chest compressions stopped for a period, thus indicating that users have switched as suggested by the defibrillator 108. Once chest compressions then start again, the defibrillator 108 may again begin determining a quality score for chest compressions provided by the new rescuer, and may indicate that rescuers should switch again when the quality falls—while all the time providing directions in the pacing of the provision of both types of compressions. In certain instances, an indication to switch may be blocked from being generated for a certain period after a new user begins performing compressions, under the assumption that the user might not be tired, but is merely trying to establish a rhythm in performing the chest compressions and abdominal compressions. Also, trends in the quality of the particular CPR component may be tracked rather than absolute values of the performance, so that the defibrillator 108 can distinguish situations in which a rescuer is giving a poor chest compressions because he or she was trying to find the appropriate rhythm or was distracted by a temporary problem, from situations in which the user truly is tiring and should be replaced.

In certain instances, the defibrillator 108 may be adaptable to different CPR protocols. For example, the defibrillator 108 may be programmed according to a protocol that, among other parameters, calls for each rescuer to provide chest compressions for a preset period of time, or calls for a different alignment of phasing as between chest compressions and abdominal compressions. In such a situation, the defibrillator 108 may use pauses in the provision of chest compressions to determine when users have switched providing chest compressions, and may start a timer based on such observation. When the timer hits the preset period, the defibrillator 108 may then provide an indication that the rescuer giving chest compressions is to change. The timer may then be reset once a next rescuer is identified as having started giving chest compressions, such as by recognizing a pause in the provision of chest compressions.

Other protocols may be more flexible and may allow switches in rescuers to be dependent on the performance of the rescuers in addition to a predefined time interval, and to permit different phase differences to be imposed as between chest compressions and abdominal compressions. For example, the defibrillator 108 may be programmed to indicate that chest compressions are to trail abdominal compressions by 120 degrees or another appropriate value. The defibrillator 108 may also be programmed to indicate that rescuers should change when it senses that performance has fallen below an acceptable level, and may also indicate the need for change when a maximum preset time has occurred even if the current rescuer appears to be performed well. In such a protocol, the time interval may be substantially longer than an interval for a protocol that requires changing based only upon elapsed time, and not upon degraded performance by the rescuer. Various different protocols may call for changing of rescuers based on different levels in performance, or upon different elapsed time periods, or a combination of the two. In particular, AHA protocols are generally just guidelines, and a particular medical director may alter such guidelines to fit their particular needs or professional judgment. (Indeed, revisions to AHA guidelines typically come from forward-thinking people who make modifications to prior guidelines and find the modifications to be effective.)

In such a situation, the defibrillator 108 may be programmed with the parameters for each of the protocols, and an operator of the defibrillator 108 may select a protocol to be executed by the defibrillator 108 (or the protocol may have been selected by a medical director). Such a selection may occur at the time of a rescue, or at a prior time. For example, the ability to select of a protocol may be limited to someone who logs onto the defibrillator 108 or configuration software separate from defibrillator 108 using administrator privileges, such as a person who runs an EMT service (e.g., a medical director of appropriate training and certification to make such a determination). That person may select the protocol to be followed on each of the machines operated by the service, and other users may be prevented from making such changes. In this manner, the defibrillator 108 may be caused to match its performance to whatever protocol its users have been trained to.

Thus, using the techniques described here, the defibrillator 108 may, in addition to providing defibrillation shocks, ECG analysis, and other features traditionally provided by a defibrillator, also provide indications to coordinate provision of chest compressions with provision of abdominal compressions, and to switch rescuers between various components of providing CPR and other care to a patient. The defibrillator may be deployed in the same manner as are existing defibrillators, but may provide additional functionality in a manner that can be easily understood by trained and untrained rescuers.

Although the above description focuses on chest compression and abdominal compression, other rescuer activities may also be monitored and prompted in a coordinated fashion. For example, a mechanical ventilation device may be provided at the patient's mouth to provide positive and/or negative ventilation to the patient in addition to, or instead of, the use of abdominal compressions. The timing of such ventilation may be coordinated with the timing of the chest compressions in an out-of-phase manner (e.g., out of phase by about 90 or 270 degrees) so as to achieve the benefits of better lung circulation and less sloshing discussed above and below.

Each of the techniques discussed here for prompting manual chest compression and abdominal compression may also be carried out automatically in a device that mechanically provides chest compression and abdominal compression or decompression, e.g., by a computer controller in a medical device triggering mechanical devices such as electric motors and/or pneumatic pumps or valves to actuate the motion of components that perform such actions on a patient. Examples of such devices are discussed next.

FIGS. 2A and 2B show a side view of a patient being treated by mechanisms for performing coordinated chest compressions and abdominal-based ventilations. In these examples, FIG. 2A shows a device that uses two belts 206, 212 to perform compression of the chest and abdomen in a coordinated manner, whereas FIG. 2B shows the use of a belt 206 for chest compression and a cuirass for abdominal decompression. The discussions above and below about coordinated approaches applies equally to each instances, unless clearly inappropriate, and generally with the opposite affect for decompression as opposed to compression.

Referring now more particularly to FIG. 2A, there is shown a medical device 200 having a backboard 204 onto which may be placed a patient 202, such as a person who is suffering from cardiac arrest (the arm of the patient has been truncated in the figure so as to better show the components of the device 200). The backboard 204 has attached to it a chest compression belt 206, which may be formed from two belt segments that may open in front of the patient's 202 chest, wrapped over the top of the patient, and secured via hook-and-loop fasteners on each of the segments that engages with hook-and-loop fasteners on the other segment.

The two segments of the belt 206 may be joined to an actuator in the backboard 204, such as to a spindle that is connected to a stepper motor controller by a computer controller (not shown). The stepper motor may cause the spindle to rotate and the belt segments (which may be joined in a single belt under the patient and at the spindle) to wrap around the spindle and thus shorten in length around the chest of the patient 202. In this manner, the device 200 may operate like an AUTOPULSE from ZOLL Medical Corp. of Chelmsford, Mass.

A second belt 212 may be positioned further down the backboard 204, closer to the patient's feet. This belt 212 may also include two segments that are attached to a spindle in the backboard 204 for shortening and releasing the belt segments so as to induce compression in the abdominal region. The spindle for belt 212 may be operated via a second stepper motor or from the same motor as belt 206, where the mechanisms for moving the spindles may be connected by a mechanical linkage that may be able to provide an appropriate amount of phase delay for coordinating the motion of the two belts in the manners discussed above and below (e.g., in FIG. 3). Also, one or more of belts 206 and 212 may be repositionable along the length of the backboard 204 so as to accommodate patients of varying torso length. For example, the spindle for belt 212 may be slidable along the length of the backboard 204 by up to several inches, and the belt 212, where it bends around the corner of the backboard 204, may pass around additional metal spindles that allow the belt to slide easily as it is contracted and released. A rescuer may then adjust the position of the belt 212 easily along the length of the backboard 204 so as to match the relative dimensions of the particular patient 202, who may be tall or short or in between.

In use then, the device 200 can be deployed from an ambulance and laid on the floor or ground next to a patient. Rescuer's may pull apart the belt segments for belt 206 and belt 212, and lay them spread outward from the backboard 204 on each side of the backboard 204. The rescuers may then move the patient 202 into position on top of the backboard 204, laying on their back as shown in the figure. The rescuers may position the patient so that the belt 206 is positioned properly relative to the patient's chest, and may close the belt segments in an overlapping manner over the patient's chest so that the belt 206 is snug. The belt segments may be held in this manner by the hook-and-loop fasteners that cover opposed surfaces of the respective belt segments. The rescuers may them slide the belt segments for belt 212 longitudinally along the backboard 204 so that they are positioned below the patient's 202 diaphragm and rib cage, and may secure the belt 212 in the same manner as the belt 206 was secures.

A rescuer may then activate the device 200, such as by turning on power to the device—e.g., via a switch on device 200, or from a separate device, such as a defibrillator or computer (e.g., tablet computer) that is used to control operation of the device 200. Such activation may cause the device to begin applying coordinated compressions to belts 206 and 212, such as in manners discussed above and below. For example, belt 212 may initially begin a compression, and belt 206 may begin its compression a fraction of a second thereafter, before the belt 212 has released from its compression, and possible while the belt 212 is still increasing its level of compression. Each belt may also include a dwell period and a release period when the tension on the belt segments is released, and those period may be the same for each of belt 206 and belt 212, or can be different. The phase difference, the period of each cycle, the rate of compression and decompression, the distance of the compressions, and the time for each phase of a cycle may be set by a manufacturer, and in certain circumstances may be adjusted by a medical director for a particular emergency service, or even in the field by the rescuers.

FIG. 2B shows a similar device 200, but here the belt 212 has been replaced by a cuirass 208 and pneumatic tube 210 for driving the cuirass 208. The backboard 204 and belt 206 interact as discussed above, and operate as discussed above. The cuirass may include a plastic shield that lays across and seals to the patient's abdomen, and as such, would not break at the midline of the patient's body, as did the belt 212. Rather, the cuirass 208 may be set entirely to one side of the backboard 204 initially, and then swept over the patient's abdomen when they are in position, with straps on one side of the cuirass being initially free of connection, but then connected on an opposite side of the backboard 204. A rescuer may initially apply the cuirass at an appropriate level of snugness around the patient, or the straps that hold the cuirass may be attached to a motor that then snugs them up after the rescuer has completed the attachment.

The cuirass may then be operated in a well-known manner, but in the coordinated manner described above and below. In particular, positive and negative pressure may be created via pneumatic tube 210, where positive pressure will compress the abdomen, push the diaphragm upward, and push air out of the patient's lungs, and negative pressure will do effectively the opposite.

In this manner, the mechanical device may result in optimized blood flow through a patient receiving CPR chest compressions through various phases of the chest compressions. Blood flow into the lungs and the torso may be increased by such coordination, and sloshing of the blood without effective circulation may be reduced.

Figure 3:
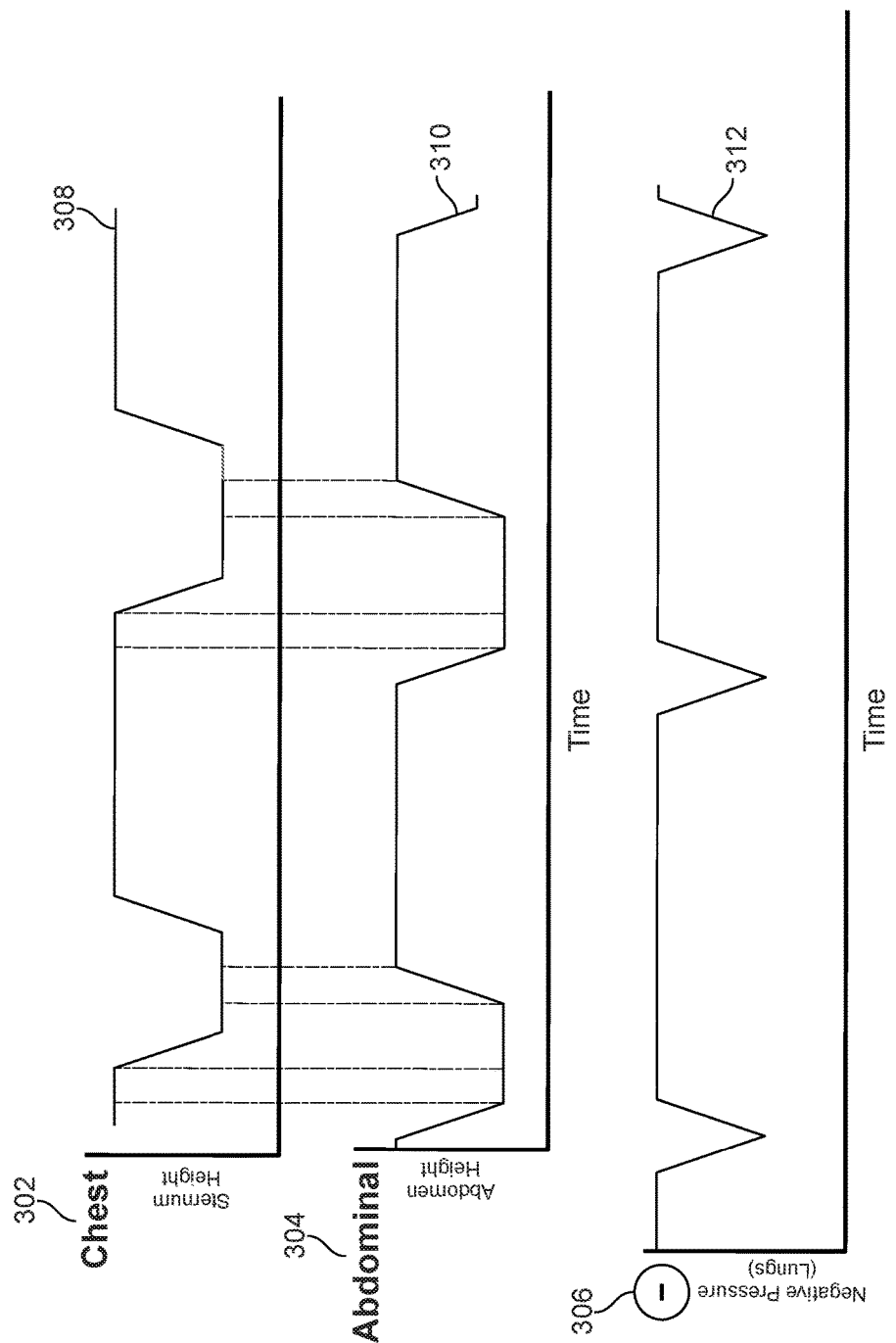
FIG. 3 shows timing diagrams for the application of coordinated chest and abdominal compressions during CPR.

FIG. 3 shows timing diagrams for the application of coordinated chest and abdominal compressions during CPR. The diagram has three parts: one for the timing of chest compressions 302, one for the timing of abdominal compressions 304, and one for ventilation 306.

Referring more particularly to the graph for chest compressions 302, a line 308 shows the height of the patient's sternum relative to time. The timeline shows a little more than two complete compression and release cycles, and if one assumes a rate of over 100 compressions per minutes, the total length of the 2 cycles is between 1 and 2 second. The compression line (moving from a high value to a low value) and the decompression line both have a non-infinite slope, so as to indicate that a rescuer or mechanical device cannot perform a compression immediately, due to resistance provided by the patient's body. The horizontal lower line segment indicates a brief dwell time in the compression, though the flatness of the line is somewhat idealized. There is then a relatively long (though around ½ second) pause before the next compression occurs.

The graph of abdominal compression 310 is similar but leads the graph of chest compression 308 slightly. In particular, the rates of the two graphs effective match each other (e.g., over a period of multiple compressions they, will be at the same average rate, and will vary for most individual particular compression cycles by less than 30%), and the dashed lines between them indicate that the abdominal compression leads by about 90 degrees. Such phase different may be different in particular applications, and will be a value that improves blood flow from the coordinated compressions relative to uncoordinated compressions or to compressions that are in phase or 180 degrees out of phase. Particular phase differences can be about 30 degrees to about 150 degree, in a positive or negative direction between the two types of compressions (and depending on whether abdominal compression is being tracked or abdominal decompression).

The ventilation graph 306 includes a line 312 showing the change in negative pressure in a patient's lungs during the compressions. The data here does not match classic ventilation rates (generally 6-10 breaths per minute), but instead shows that the coordinated chest and abdominal compressions can affect internal lung pressure.

Figure 4:
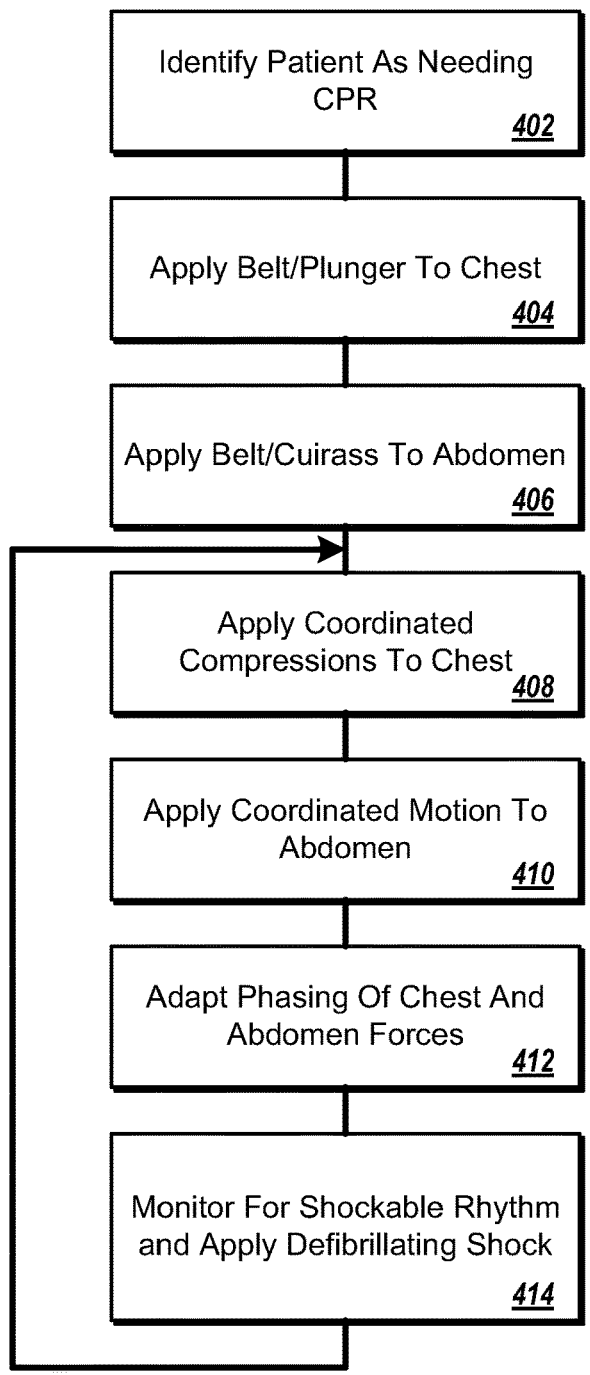
FIG. 4 is a flowchart of a process for performing coordinated CPR.

FIG. 4 is a flowchart of a process for performing coordinated CPR. In general, the process involves applying coordinate chest and abdominal compressions to a patient as part of CPR.

The process begins at box 402, where a patient in need of CPR is identified. Such identification may occur, for example, by a civilian seeing another person undergoing what appears to be cardiac arrest (e.g., the person is lying pronate and unconscious). Such a civilian may then take appropriate steps to determine that the person needs CPR and related life-saving measures. Alternatively, a rescuer such as an EMT may be called by a dispatcher and may drive to the scene of someone who has been reported as needing emergency attention, such as via a third-party calling a 911 service.

At box 404, a belt or, plunger or similar compression device is applied to the chest of the person, not referenced as a patient (whether the rescuer is a layperson or a healthcare professional) because they are in need of medical assistance. For example, where the chest compression device is in the form of a belt like that shown in FIGS. 2A and 2B, the rescuer can place the patient on a backboard, and secure the belt snugly around the patient. The medical device may then further snug the belt to a predetermined degree, and may do so automatically upon being actuated by a rescuer. Where the chest compression mechanism is a plunger, the plunger may be attached to a gantry that extends over the patient, or can be on the inside of a belt that is wrapped around the patient. Again, the mechanism may be automatically positions against the patient's chest in a manner that it is ready to begin giving accurate chest compressions to the patient.

At box 406, a belt, cuirass, or similar mechanism is positioned relative to the patient's abdomen. Where the mechanism is a belt, like in FIG. 2A above, it may be wrapped around the patient and two portions of the belt may be joined together above the patient's abdomen. The belt may then be snugged against the patent automatically upon the user activating the device to do so. Where the mechanism is a cuirass, the rescuer may remove the patient's shirt and seal the shell of the cuirass against the patient's abdomen, and may also tighten the shell to the patient, such as using straps that attach to a backboard placed under the patient, as shown above for FIG. 2B. At this stage, the rescuer may check the patient and the set-up of the device to confirm that each of the mechanisms is properly positioned and ready to treat the patient. The rescuer may then activate the medical device to begin providing coordinated compressions and/or decompressions to the patient's chest and abdomen. Thus, at box 408, coordinated compressions are applied to the chest, and at box 410, coordinated motion is applied to the abdomen, where the coordination refers to coordination in timing of the motion induced in the chest as compared to the motion induced in the abdomen. Such coordination may occur in the offset of the cycles as between the chest and abdomen, such as explained above and shown in FIG. 3.

At box 412, the phasing or other parameters of the chest and abdomen compressions are adaptively changed. For example, blood flow in the patient at particular locations may be measured, and determinations may be made whether the chest compressions are providing adequately blood flow. If the blood flow falls from earlier in the process, changes can be made to the relative phasing of the chest and abdomen compressions, the compress and release velocities for either may be changed, the depths may be changed, or the dwell times can be changed. Such changes may be made according to predetermined formulae or similar mechanisms, or in response to trial and error. In the former circumstance, it may be known that chest compressions that go deeper must be provided later in a rescue than earlier, and thus a medical device may be set to automatically provide deeper compressions after operating for a time. For the latter circumstance, the relative phasing of the compressions may be changed in one direction by an amount, such as by 5 or 10 degrees. The device may then measure the relative change in blood flow from such a change, and may maintain the changed phasing if the result was positive (e.g., better circulation), and return to the old phasing if the result was negative.

Simultaneous with providing the mechanical inputs discussed here, a device or system may monitor the patient for a shockable rhythm, for purposes of determining whether to deliver a defibrillating shock to the patient. Such monitoring is common with portable defibrillators and may make a determination that such a rhythm exists by using monitoring electrodes that are part of a defibrillator electrodes system placed across the patient's chest. If such a rhythm exists, a capacitor may be charged in the device, the rescuers may be notified and warned to move back from the patient, and then instructed to press a button to cause the shock to be delivered. Each of the steps for performing the operations on the patient may then be repeated until the patient is capable of existing without the additional help.

Figure 5:
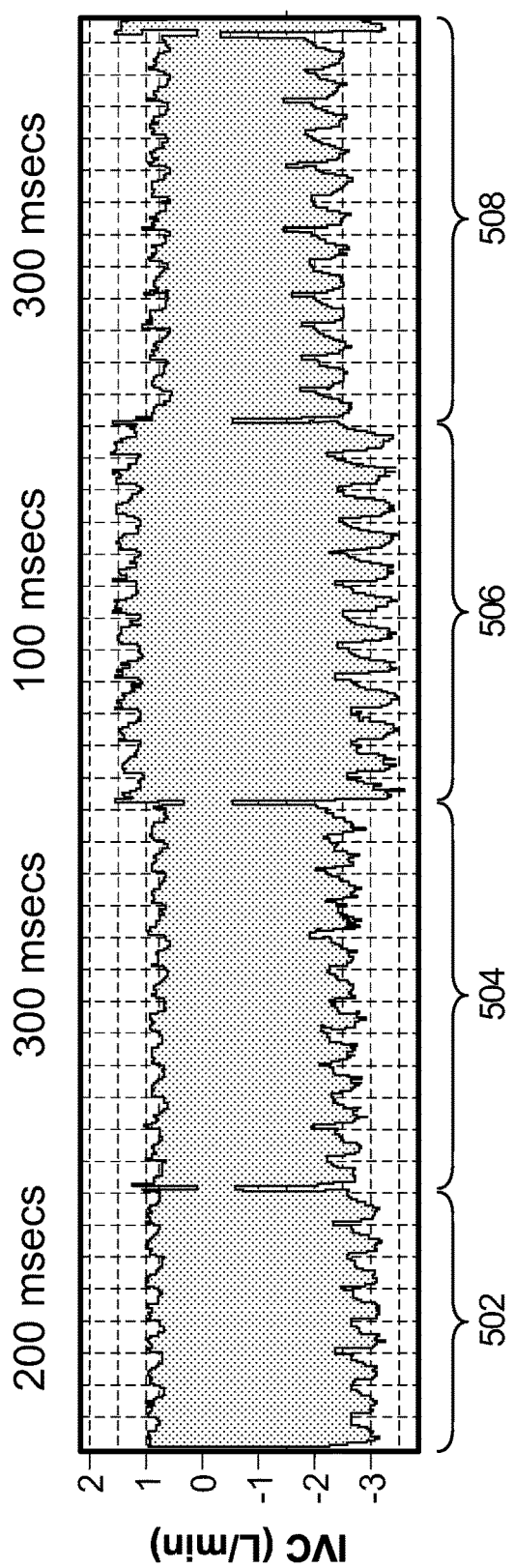
FIG. 5 is a chart showing blood flow at varying chest compression release velocities.

FIG. 5 is a chart showing blood flow at varying chest compression release velocities. The chart generally shows that blood flow increases for increasing release velocity, but that overall effectiveness of the compressions may not increase because the increased flow occurs in the form of sloshing rather than effective circulatory flow. Such sloshing may be lessened using the coordinated compression techniques discussed above.

Referring more particularly to the chart, zone 502 shows multiple compressions and release performed using a 200 msec release velocity, and the blood volume in liters per minute is 1 positive and 3 negative. The main relevance of such data is to show that there was significant sloshing (a period of peak forward flow followed by another period of significant backward flow). Later, in zone 504, the release velocity was decreased so that the release required 300 msec. The volume fell slightly but not an appreciable amount. Later, in zone 506, the velocity was increased to 100 msec, and the volume increase was significant, but did so in both positive and negative direction—showing that in this example, increase velocity led to sloshing of blood in the test subject. And in zone 508, the administration of compressions returned to a 300 msec rate, and the volumes were similar to those in zone 504 again.

That data shown here were obtained from a study of eight domestic swine (~30 kg) using standard physiological monitoring. A flow probe was placed on the inferior vena cava. Ventricular fibrillation was electrically induced. Mechanical chest compressions were provided by a device that provided consistent sternal compressions. Chest compressions were started after ten minutes of untreated ventricular fibrillation. The chest compression release time was adjusted so that sternal recoil lasted 100 ms, 200 ms, or 300 ms. Chest compressions were delivered over 54 min at a rate of 100 per minute and at a depth of 1.25 in.

The particular techniques described here may be assisted by the use of a computer-implemented medical device, such as a defibrillator that includes computing capability. Similarly, the computing features discussed here may be included in a back board like that shown in FIGS. 2A and 2B to control coordinated actuation of chest compression and abdominal movement devices in manners like those discussed above.

Figure 6:
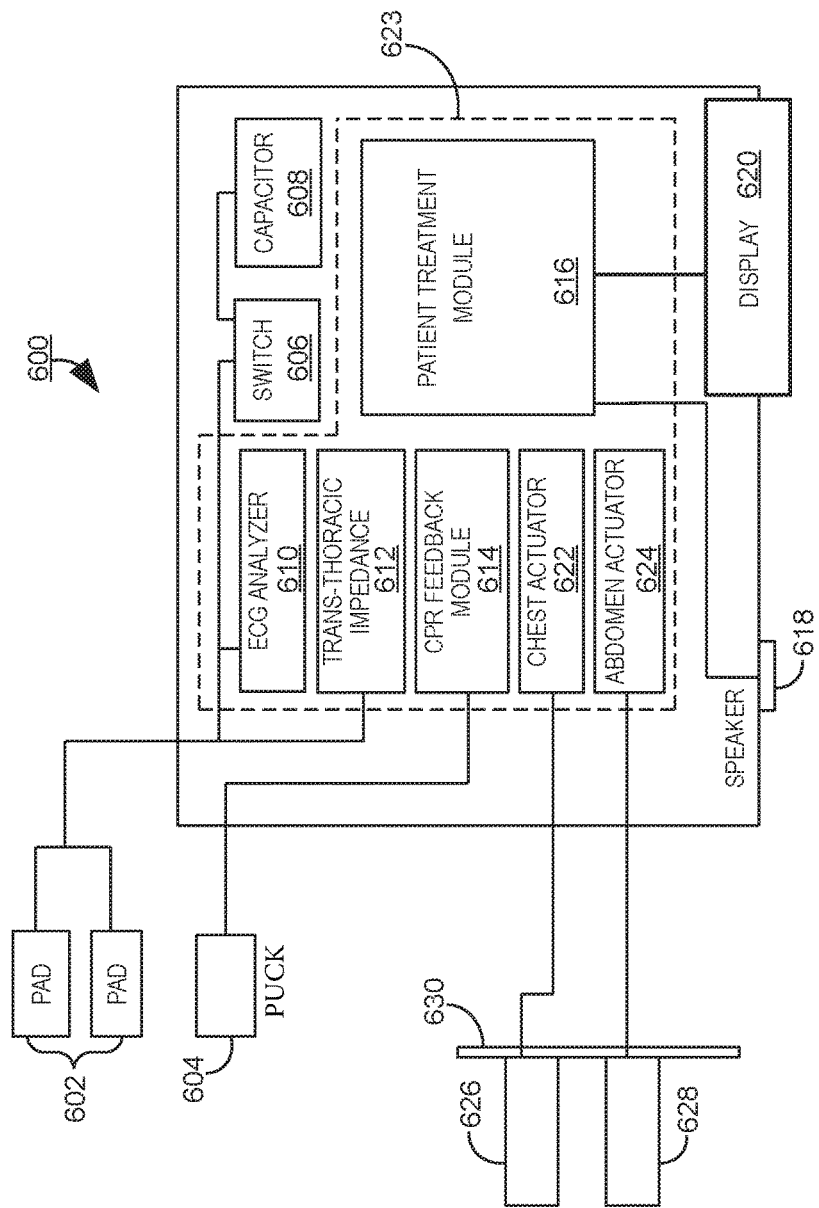
FIG. 6 is a schematic block diagram that shows a defibrillator with an electronic controller for providing automated CPR-related interaction.

Referring now to FIG. 6, a schematic block diagram 600 shows an example defibrillator system 600, along with an example electrode package 602 and compression puck 604. The defibrillator system is also provided with a back board 630 having a machine-actuated chest compression belt 626 and machine-actuated abdomen compression belt 628. In general, the defibrillator system 600 defines an apparatus or collection of apparatuses for administering care to a patient who requires cardiac assistance.

Particular example components are shown in the defibrillator system 600 to assist a rescuer with the provision of such care to a patient. For example, the defibrillator 600 includes a switch 606 and at least one capacitor 608 for selectively supplying or applying a shock to a subject. The defibrillator 600 further includes an ECG analyzer module 610, a trans-thoracic impedance module 612, a CPR feedback module 614 that controls frequency and magnitude of chest compressions applied to a subject, a patient treatment module 616, a speaker 618, and a display 620. In this example, the ECG analyzer module 610, trans-thoracic impedance module 612, CPR feedback module 614, and patient treatment (PT) module 616 are grouped together as an electronic controller 623, which may be implemented by one or more computer processors. For example, respective elements of the electronic controller can be implemented as: (i) a sequence of computer implemented instructions executing on at least one computer processor of the defibrillator system 600; and (ii) interconnected logic or hardware modules within the defibrillator system, 600, as described in further detail below in connection with FIG. 7.

In the example of FIG. 6, the electrode package 602 is connected to the switch 606 via a port so that different packages may be connected at different times. The electrode package 602 may also be connected through the port to ECG analyzer module 610, and trans-thoracic impedance module 612. The compression puck 604 is connected, in this example, to the CPR feedback module 614. In one embodiment, the ECG analyzer module 610 is a component that receives an ECG signal. Similarly, the trans-thoracic impedance module 612 is a component that receives transthoracic impedance signals that may be used in making determinations about when a shock can and should be delivered to a patient. Other embodiments are possible.

Separately, a chest actuator 622 and abdomen actuator 624 may be provided as part of the electronic controller 623. Though shown for illustration here as entirely in the electronic controller 623, in actual implementation, they may include relays or other actuator structures external to a processor, in addition to functionality for making determinations for actuating such structures. For example, as discussed above, the electronic controller may be programmed to implement automatic contraction and release of belts 626 and 628 in an off-phase relationship so as to improve circulation provided by chest compressions. Also, such actuating structures may be provided in a device that is physically separate from a defibrillator, such as in the back board 630, which may communicate wirelessly with the defibrillator. In addition, the timing determinations made by the chest actuator 622 and abdomen actuator 624 may be output in other ways, such as via pacing sounds delivered to speaker 618 and feedback information delivered to display 620, in manners like those discussed above. In certain implementations in which the chest belt 626 is provided, the puck 604 may be unnecessary.

The patient treatment module 616 is configured to receive an input from each one of the ECG analyzer module 610, trans-thoracic impedance module 612, and CPR feedback module 614. In addition, the patient treatment module may also receive input about the positions of belts 626 and 628, or the state of actuation of the belts 626, 628. The patient treatment module 616 uses inputs as received from at least the ECG analyzer module 610 and trans-thoracic impedance module 612 to predict whether a defibrillation event will likely terminate an arrhythmic episode. In this manner, the patient treatment module 616 uses information derived from both an ECG signal and transthoracic impedance measurement to provide a determination of a likelihood of success for delivering a defibrillating shock to a subject.

The patient treatment module 616 is further configured to provide an input to each one of the speaker 618, display 620, and switch 606. In general, input provided to the speaker 618 and display 620 corresponds to either a success indication or a failure indication regarding the likelihood of success for delivering a shock to the subject. In one embodiment, the difference between a success indication and a failure indication is binary and based on a threshold. For example, a success indication may be relayed to the display 620 when the chances corresponding to a successful defibrillation event is greater than 75%. In this example, the value "75%" may be rendered on the display 616 indicating a positive likelihood of success. When a positive likelihood of success is indicated, the PT module 616 enables the switch 606 such that a shock may be delivered to a subject. In another embodiment, likelihood of a successful defibrillation event may be classified into one of many possible groups such as, for example, low, medium, and high likelihood of success. With a "low" likelihood of success (e.g., corresponding to a successful defibrillation event is less than 50%), the PT module 616 disables the switch 606 such that a shock cannot be delivered to a subject. With a "medium" likelihood of success (e.g., corresponding to a successful defibrillation event is greater than 50% but less than 75%), the patient treatment module 616 enables the switch 606 such that a shock may be delivered to a subject, but also renders a warning on the display 620 that the likelihood of success is questionable. With a "high" likelihood of success (e.g., corresponding to a successful defibrillation event is greater than or equal to 75%), the patient treatment module 616 enables the switch 606 such that a shock may be delivered to a subject, and also renders a cue on the display 620 indicating that the likelihood of success is very good. Still other embodiments are possible.

The patient treatment module 616 may also be configured to provide an input to each one of the speaker 618, display 620, and switch 606, to present indications that show the status of chest and/or abdominal compressions being provided mechanically or manually to the patient, or to prompt such actions when they are being performed manually. For example, the patient treatment module may be programmed to prompt actuation of belts 626, 628 or to prompt human rescuers to provide chest and/or abdomen compressions in an phase-offset manner in the ways discussed above, such as by speaking timed commands to cause rescuers to provide treatment to a patient in time and properly out-of-phase.

Figure 7:
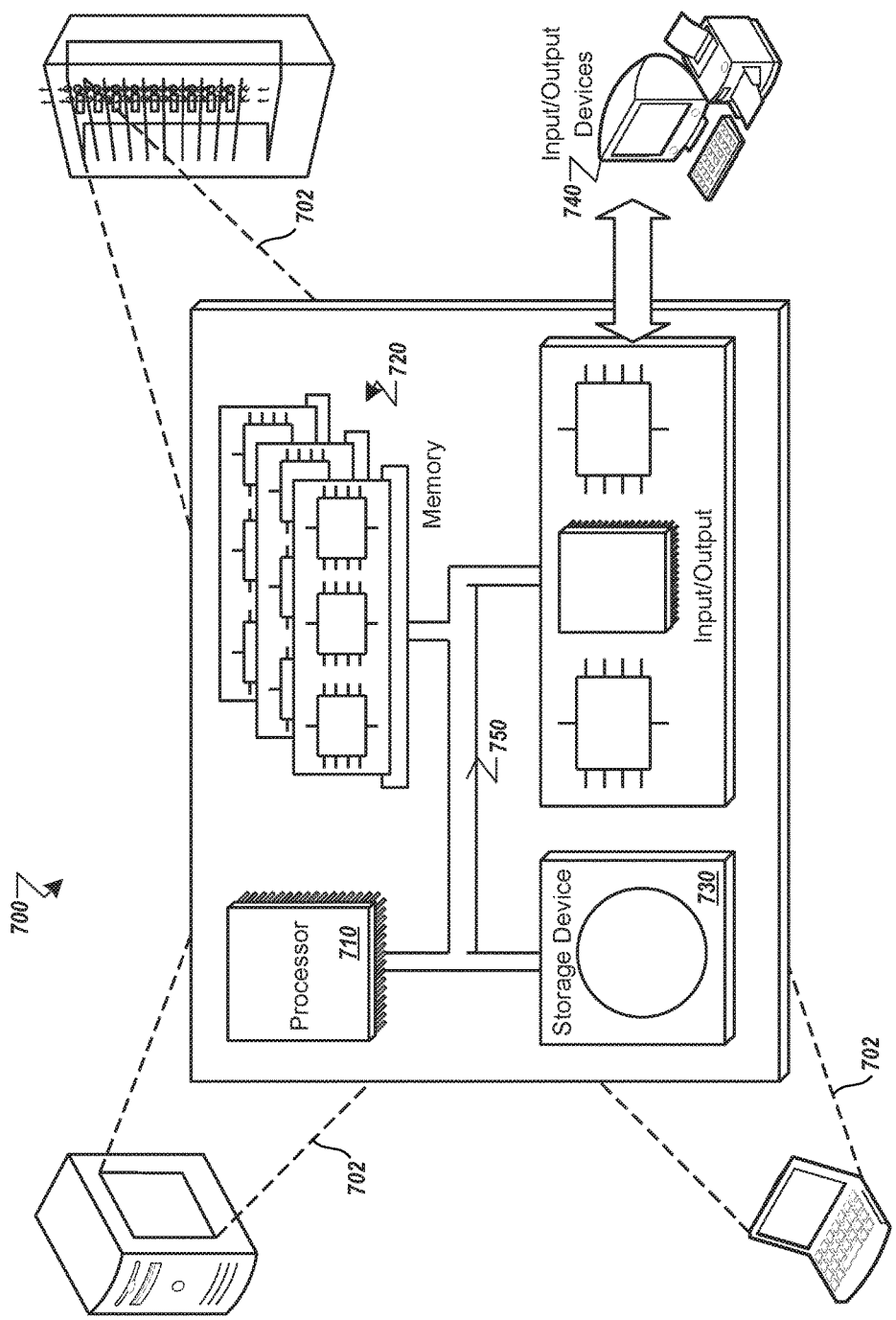
FIG. 7 shows an example of a computer device that can be used to implement the techniques described here.

FIG. 7 is a schematic diagram of a computer system 700. The system 700 can be used for the operations described in association with any of the computer-implement methods described previously, according to one implementation. The system 700 is intended to include various forms of digital computers, such as laptops, desktops, workstations, personal digital assistants, servers, blade servers, mainframes, and other appropriate computers connected by a communication network 702 system. The system 700 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. The processor may be designed using any of a number of architectures. For example, the processor 710 may be a CISC (Complex Instruction Set Computers) processor, a RISC (Reduced Instruction Set Computer) processor, or a MISC (Minimal Instruction Set Computer) processor.

In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A system for providing emergency care to a patient, the system comprising:
   a backboard arranged to support the patient;
   a chest compressor attached to the backboard and positioned to engage the patient at the chest, the chest compressor configured to provide multiple chest compression cycles to the patient, wherein the multiple chest compression cycles are configured to provide a compression of the sternum to a compressed sternal position followed by a hold of the sternum in the compressed sternal position followed by a release of the sternum from the compressed sternal position;
a cuirass attached to the backboard and positioned to engage the patient at the abdomen, the cuirass configured to generate negative pressure to pull outward on the abdomen and to provide multiple abdominal compression cycles to the patient wherein the multiple abdominal compression cycles are configured to provide a compression of the abdomen to a compressed abdominal position followed by a hold of the abdomen in the compressed abdominal position followed by a release of the abdomen from the compressed abdominal position; and
a defibrillator comprising one or more processors configured to:
control the chest compressor to perform the multiple chest compression cycles and the cuirass to perform the multiple abdominal compression cycles according to a programmed sequence such that the compression of the sternum to the compressed sternal position occurs during the hold of the abdomen in the compressed abdominal position and after the compression of the abdomen to the compressed abdominal position and such that the release of the sternum from the compressed sternal position occurs over a pre-determined time interval, and
control the cuirass to generate the negative pressure to pull outward on the abdomen prior to the compression of the abdomen to the compressed abdominal position.

2. The system of claim 1, wherein the one or more processors are further configured to control the performance of the multiple chest compression cycles and the multiple abdominal compression cycles according to the programmed sequence such that an average rate of the multiple chest compression cycles is approximately equal to an average rate of the multiple abdominal compression cycles.

3. The system of claim 1, wherein the one or more processors are further configured to control the performance of the multiple chest compression cycles and the multiple abdominal compression cycles according to the programmed sequence such that each compression of the sternum to the compressed sternal position begins when an ongoing abdominal compression cycle of the multiple abdominal compression cycles is about one-quarter complete.

4. The system of claim 1, wherein the one or more processors are further configured to control the performance of the multiple chest compression cycles and the multiple abdominal compression cycles according to the programmed sequence such that each chest compression cycle of the multiple chest compression cycles is performed approximately 90 or 270 degrees out of phase with an ongoing abdominal compression cycle of the multiple abdominal compression cycles.

5. The system of claim 1, wherein the chest compressor comprises a belt configured to be wrapped around the chest of the patient or a piston configured to press against the chest of the patient.

6. The system of claim 1, wherein the one or more processors are configured to monitor a condition of the patient while the multiple chest compression cycles are provided to the patient, and further wherein the one or more processors are configured to control an adaptive variation of parameters of one or more of the multiple chest compression cycles and the multiple abdominal compression cycles based on the monitored condition of the patient.

7. The system of claim 6, wherein the adaptive variation of the parameters comprises:
a change in a manner in which one or more of the multiple chest compression cycles and the multiple abdominal compression cycles are provided to the patient,
a measurement of a resulting change in one or more patient-dependent parameters, and
a selection of new parameters for provision of one or more of the multiple chest compression cycles and the multiple abdominal compression cycles based on the measured resulting change.

8. The system of claim 6 wherein the one or more processors are further configured to control the adaptive variation of the parameters based on blood flow measurements for the patient.

9. The system of claim 1, wherein the one or more processors are further configured to control the performance of the multiple chest compression cycles at a rate that varies by less than about 30 % compared with a rate at which the multiple abdominal compression cycles are performed.

10. The system of claim 1, wherein the one or more processors are further configured to control the performance of the multiple chest compression cycles and the multiple abdominal compression cycles according to the programmed sequence such that each chest compression cycle of the multiple chest compression cycles is about 30 degrees to 150 degrees out of phase with an ongoing abdominal compression cycle of the multiple abdominal compression cycles.

11. The system of claim 1, wherein the system further comprises at least one of a speaker or a display and further wherein the one or more processors are further configured to provide resuscitation information to a rescuer via one or more of the speaker and the display.

12. The system of claim 1 wherein the programmed sequence comprises one or more of relative phasing, compression velocity, release velocity, compression depth, and dwell time.

13. The system of claim 1, wherein the one or more processors are configured to electronically monitor one or more of an electrocardiogram (ECG) signal and a transthoracic impedance signal from the patient while the multiple chest compression cycles and the multiple abdominal compression cycles are provided to the patient.

14. The system of claim 13 wherein the one or more processors are configured to determine a likelihood of success of a defibrillation shock to the patient based on the one or more of the ECG signal and the transthoracic impedance signal.

15. The system of claim 14 wherein the one or more processors are configured to control one or more of a speaker and a display to present an indication of the determined likelihood of success of the defibrillation shock.

16. The system of claim 1 wherein the one or more processors are configured to control the chest compressor to perform the multiple chest compression cycles and the cuirass to perform the multiple abdominal compression cycles according to the programmed sequence such that the release of the abdomen from the compressed abdominal position occurs during the hold of the sternum in the compressed sternal position and before the release of the sternum from the compressed sternal position.

17. The system of claim 1 wherein the release of the sternum from the compressed sternal position over the pre-determined time interval corresponds to a release velocity characterized by a non-infinite slope on a graph of sternum displacement as a function of time.

18. The system of claim 17 wherein the pre-determined time interval is in a range from 100 msec-300 msec.

19. The system of claim 1,
wherein the backboard comprises a pneumatic power mechanism and a motor coupled to the pneumatic power mechanism and configured to cyclically drive the pneumatic power mechanism to control the cuirass in response to control signals from the one or more processors, and
wherein the cuirass comprises a shell and a pneumatic tube coupled to the shell and configured to couple to the pneumatic power mechanism.

20. The system of claim 19, wherein the pneumatic power mechanism is configured to generate a positive pressure inside the shell via the pneumatic tube to compress the abdomen.

21. The system of claim 19 wherein the pneumatic power mechanism is configured to generate the negative pressure inside the shell via the pneumatic tube to pull outward on the abdomen.

22. The system of claim 19 wherein the chest compressor comprises a belt and wherein the motor is configured to cyclically drive the belt in response to signals from the one or more processors to provide the multiple chest compression cycles to the patient.

23. The system of claim 19 wherein the cuirass comprises straps configured to connect to the motor and wherein the motor is configured to move the straps to tighten the cuirass against the abdomen of the patient.

24. The system of claim 1 wherein the cuirass comprises a mechanical compression element configured to compress the abdomen.

* * * * *

UNITED STATES PATENT AND TRADEMARK OFFICE
CERTIFICATE OF CORRECTION

PATENT NO. : 10,188,582 B2
APPLICATION NO. : 13/970051
DATED : January 29, 2019
INVENTOR(S) : Gary A. Freeman and Christopher Luke Kaufman It is certified that error appears in the above-identified patent and that said Letters Patent is hereby corrected as shown below:

In the Specification

Column 19, Line 7, delete "702 system.", insert -- 702. --

Signed and Sealed this
Second Day of April, 2019

Andrei Iancu
*Director of the United States Patent and Trademark Office*